US011839496B2

(12) United States Patent
McCord et al.

(10) Patent No.: US 11,839,496 B2
(45) Date of Patent: Dec. 12, 2023

(54) MONITORS FOR MOVEMENTS OF WORKERS

(71) Applicant: JointAction Group Pty Ltd, Dee Why (AU)

(72) Inventors: Roscoe McCord, Dee Why (AU); Michael Lawrance, Dee Why (AU); Steven Cowley, Dee Why (AU); David Bick, Dee Why (AU); John Pryor, Dee Why (AU)

(73) Assignee: JOINTACTION GROUP PTY LTD, Dee Why (AU)

( * ) Notice: Subject to any disclaimer, the term of this patent is extended or adjusted under 35 U.S.C. 154(b) by 1036 days.

(21) Appl. No.: 16/452,288

(22) Filed: Jun. 25, 2019

(65) Prior Publication Data
US 2020/0000414 A1   Jan. 2, 2020

(30) Foreign Application Priority Data
Jun. 27, 2018   (AU) .............................. 2018204669

(51) Int. Cl.
*A61B 5/00* (2006.01)
*A61B 5/11* (2006.01)
*G06N 20/10* (2019.01)
*G16H 50/30* (2018.01)
*G06V 40/13* (2022.01)

(52) U.S. Cl.
CPC .......... *A61B 5/7275* (2013.01); *A61B 5/1114* (2013.01); *A61B 5/1118* (2013.01); *A61B 5/1126* (2013.01); *A61B 5/7267* (2013.01); *G06N 20/10* (2019.01); *G06V 40/13* (2022.01); *G16H 50/30* (2018.01); *A61B 2503/20* (2013.01); *A61B 2562/0219* (2013.01)

(58) Field of Classification Search
None
See application file for complete search history.

(56) References Cited

U.S. PATENT DOCUMENTS

| 2017/0169687 A1* | 6/2017 | Kozloski ................ G08B 21/02 |
| 2017/0245806 A1* | 8/2017 | Elhawary ............. A61B 5/1122 |
| 2019/0224528 A1* | 7/2019 | Omid-Zohoor ...... A61B 5/0024 |
| 2019/0269970 A1* | 9/2019 | Canavan ............. A61B 5/6831 |
| 2019/0283247 A1* | 9/2019 | Chang .................. A61H 1/0237 |
| 2019/0295436 A1* | 9/2019 | Rubinstein ........... A61B 5/1121 |
| 2019/0295437 A1* | 9/2019 | Rubinstein ............. A61B 5/742 |

(Continued)

*Primary Examiner* — Benjamin S Melhus
(74) *Attorney, Agent, or Firm* — LEWIS ROCA ROTHGERBER CHRISTIE LLP

(57) ABSTRACT

This disclosure relates to a sensor-based monitor for movements of workers. Multiple inertial sensors are attached to different body parts of the workers. A mobile device application receives the inertial movement data from the sensors and identify movement patterns by applying a trained machine learning model to the inertial movement data. The application then determine for each movement pattern an amount of time that movement pattern occurred and accessing a database to retrieve stored data on an association between the identified movement patterns and injuries. The application calculates a risk value indicative of a risk of injury of the worker as a result of performing the identified movement pattern for the determined amount of time and produces a report detailing the risk value for each of multiple risk categories.

17 Claims, 6 Drawing Sheets

(56) References Cited

U.S. PATENT DOCUMENTS

| | | | |
|---|---|---|---|
| 2019/0295438 A1* | 9/2019 | Rubinstein | G09B 5/06 |
| 2019/0343429 A1* | 11/2019 | Elhawary | A61B 5/6823 |
| 2019/0347597 A1* | 11/2019 | Asendorf | H04B 1/385 |
| 2021/0233654 A1* | 7/2021 | Arthur | G06Q 10/063114 |
| 2021/0236020 A1* | 8/2021 | Matijevich | A61B 5/7455 |

* cited by examiner

MONITORS FOR MOVEMENTS OF WORKERS

CROSS-REFERENCE TO RELATED APPLICATION(S)

This application claims priority to Australian Patent Application Number 2018204669, filed on Jun. 27, 2018, the entire contents of which are incorporated herein by reference.

TECHNICAL FIELD

This disclosure relates to a sensor-based monitor for movements of workers.

BACKGROUND

Machine learning has become a powerful tool for gaining insights into large datasets. For example, emails are being classified as spam or non-spam after a supervised training process where human users tag emails manually as spam/non-spam. A machine learning model is then trained using these learning samples, which means parameters are being calculated that best describe the statistical occurrence of particular words, phrases or meta-data values in spam and non-spam emails. The trained machine learning model can then be applied to non-classified, newly received emails to filter out the spam emails.

While the supervised training approach has been successfully applied in some areas, there are also serious difficulties with this approach in others. Most importantly, in many cases there are a large number of features (i.e. input variables) such as different words, which may all be an indicator for the classification, which leads to the known "curse of dimensionality". In these cases, the number of training samples needs to be large in relation to the number of parameters. Otherwise, the trained machine learning model will not predict new samples accurately.

While it is not a problem to locate a large number of emails for spam training purposes, it is more difficult in other areas to find a sufficiently large number of training samples. In particular, for applications involving humans, these datasets are often not available. It may even be unethical to create these datasets. For example, in order to train a machine learning model that predicts physiological injury, a large number of injured humans is required and for each injured human the values of the training features need to be known.

It is therefore desirable, to provide a machine learning solution that achieves good prediction accuracy without the need for a large number of training samples. In other words, it is desirable to improve the currently available computer system by programming them in a way that improves these computer systems in the sense that they predict injuries accurately without a large number of injured people.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A system for monitoring movements of a worker comprises:
multiple inertial sensors attachable to different body parts of the worker to generate inertial movement data;
a mobile device application configured to
receive the inertial movement data from the inertial sensors;
identify from the inertial movement data one of multiple predefined movement patterns by applying a trained machine learning model to the inertial movement data;
determine for each movement pattern an amount of time that movement pattern occurred over a monitoring time period based on the inertial movement data;
accessing a database to retrieve stored data on an association between the identified movement patterns and injuries;
calculate a risk value indicative of a risk of injury of the worker as a result of performing the identified movement pattern for the determined amount of time and the stored data retrieved from the database for the identified movement pattern; and
produce a report detailing the risk value for each of multiple risk categories, with a graphical indication of a degree to which the identified movement pattern is performed over time.

It is an advantage that the trained machine learning model identifies the movement patterns and not the injuries directly. This is an advantage because the movement patterns can be performed by the worker without injuring the worker. This way, a large dataset can be created and the machine learning model can be trained on that large dataset. Therefore, the intermediate step of identifying movement patterns first is a technical solution to improve the accuracy of prediction using a small or non-existent learning dataset of injured workers. Further, it is generally known which movement patterns cause which injuries when these movement patterns occur over a long period of time. This information can be encoded in the database and retrieved so that the risk value is calculated based on the database information. Again, this splits the machine learning prediction into a first part of supervised learning and a second part of an expert system. This improves the data collecting device technically by splitting the internal calculations to improve the quality of the calculated result.

A method for monitoring movements of a worker comprises:
receiving inertial movement data from multiple inertial sensors attachable to different body parts of the worker to generate the inertial movement data;
identifying from the inertial movement data one of multiple predefined movement patterns by applying a trained machine learning model to the inertial movement data;
determining for each movement pattern an amount of time that movement pattern occurred over a monitoring time period based on the inertial movement data;
accessing a database to retrieve stored data on an association between the identified movement patterns and injuries;
calculating a risk value indicative of a risk of injury of the worker as a result of performing the identified movement pattern for the determined amount of time and the stored data retrieved from the database for the identified movement pattern; and producing a report detailing the risk value for each of multiple risk categories, with a graphical indication of a degree to which the identified movement pattern is performed over time.

Optional feature described of any aspect of method, computer readable medium or computer system, where appropriate, similarly apply to the other aspects also described here.

BRIEF DESCRIPTION OF DRAWINGS

An example will now be described with reference to the following drawings:

FIG. 4 illustrates a graphical indication of the degree to which each movement pattern occurred over time.

DESCRIPTION OF EMBODIMENTS

Figure 1:
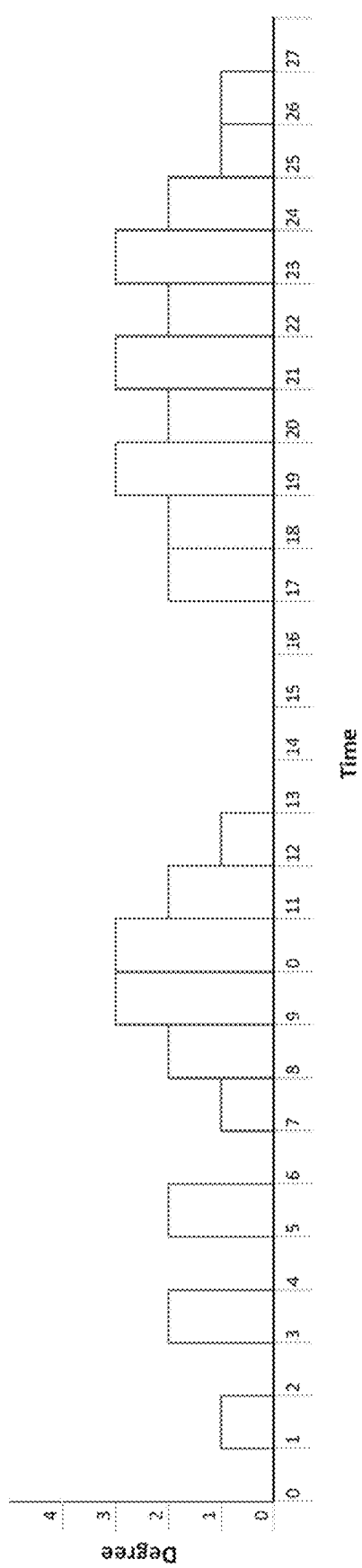
FIG. 1 illustrates a tracking state of the system.

This disclosure relates to machine learning applied to wearable sensors that obtain musculoskeletal data from workers, analyse tasks and generate scored manual handling risk assessments. The sensors deliver data to a simple-to-use app with the task for the user being to start and stop analysing the activity. The app works on phones and tablets using a developed machine learning system to analyse data and present it on intuitive screens in simple report formats.

The sensors measure acceleration and orientation, and gather data that the application uses to compute the risk assessments. The risk assessments can be shown while the task is being performed when the app is connected to the sensors, allowing real time education and training based on the assessment. The sensors can also record data on their own, without the mobile device being present, allowing automated assessments to be performed after the task has finished.

Testing in the coal production environment has proved the system and very positive feedback has been received from wearers of the sensors who report no interference with work and no discomfort. Post hoc replaying of video and risk assessment data has demonstrated the value of the system in worker engagement and manual handling solution development.

The risk assessment method employed by the application is based on and is closely aligned to the Australian Model Code of Practice-Hazardous Manual Tasks 2016 and its predecessor codes, guides and national standard. This method has been extended to address a factor that limits application by both expert and casual users; the consequence scoring in the risk estimation calculation has been populated using extensive injury clinical and claims data. This standardised method results in the provision of ranked scores based on type of injury risk and enables use alongside other Work Health & Safety risk-scoring.

There is provided a mobile application (app) that enables machine learning for low-cost, replicable, automated musculoskeletal disorder (MSD) risk assessments in the mining industry, for example.

The process involves:

Develop and prove the validity of a mobile app that uses computer learning and recognition algorithms to compute a manual handling risk assessment using data captured by wearable sensors.

Enable cost saving through an automated risk assessment process conducted by non-specialists.

Improve the consistency of MSD risk assessments across a wide variety of activities.

Collect data from a wide range of MSD risk assessments to improve knowledge transfer and guide targeted controls to reduce injury rates, and improve injury outcomes.

The sensors deliver data to a simple-to-use app with the task for the user: to start and stop analysing the activity. The app works on phones and tablets using a developed machine learning system to analyse data and present it on intuitive screens in simple report formats.

The sensors measure acceleration and orientation, and gather data that the app uses to compute the risk assessments. The risk assessments can be shown live when the mobile app is connected to the sensors when the task is being performed, allowing real time education and training based on the assessment. The sensors can also record data on their own, without the mobile device needing to be present, allowing automated assessments to be performed after the task has finished.

The risk assessment method employed by the application is based on and is closely aligned to the Australian Model Code of Practice-Hazardous Manual Tasks 2016 and its predecessor codes, guides and national standard. This method has been extended to address a factor that limits application by both expert and casual users; the consequence scoring in the risk estimation calculation has been populated using extensive injury clinical and claims data. This standardised method results in the provision of ranked scores based on type of injury risk and enables use alongside other Work Health & Safety risk-scoring.

The risk assessment process has been verified by human expert observation and assessment of the manual handling tasks being app-assessed. Satisfactory correlation of risk scores has been achieved but the differences require further investigation.

It has been found that the automated system brings a high degree of reliability to the assessment process. The measure of validity of the assessment is based on comparison with human assessment. The correlation between the app and human assessments means that risk assessment scores may be considered valid and informed choices about the necessity for risk controls may be made.

The automated musculoskeletal disorder (MSD) risk assessment system has been designed for manual handling risk assessment in the coal industry but may be applied elsewhere. Industry pilot trials have demonstrated its useability and certification for underground use is planned.

All manual handling tasks require risk assessment and the automated system will reduce costs, increase consistency of assessments and facilitate consultation on risk reduction measures. Use in the coal industry will lead to cost savings and more efficient use of health and safety and supervisor personnel's time and capacities in work related musculoskeletal disorder prevention and injury management.

The Automated Musculoskeletal Disorder Risk Assessment system for the calculation of a consequence score may be enhanced to be coal industry-specific and potentially company and site-specific with specific data to be used to provide better estimates of the costs of risk and cost benefit of risk controls under consideration.

Wearable motion sensors incorporating an accelerometer, magnetometer and gyroscope have been available commercially for some time and are used in the sports sciences. Adoption of these for use in musculoskeletal risk assessments in the coal industry required development of algorithms that would firstly enable aggregation of orientation data from multiple sensors and secondly the translation of that aggregated sensor data to information that can be related to manual handling risk phrases. Simultaneously it was necessary to develop a consequence scoring system that could be combined with the risk phrase scoring to deliver an overall risk score.

In one example, commercially available sensor hardware may deliver sufficient accuracy to compute absolute orientation and, in turn, record and stream the captured data to an app. It was found that commonly used mobile devices had sufficient processing capability to interpret and analyse the incoming data in real-time.

It was acknowledged that an advantage of a commercial application would be ease-of-use in the field. As such, a determination was made that the sensor units communicate their data (either streaming, or sending after recording it internally) with the receiving mobile device via the Bluetooth LE protocol. Bluetooth LE requires no complicated pairing (eliminating problems with the sensors being paired to the wrong device), is very power efficient (allowing the sensors to stream data to the mobile device all day) and allows several devices to be connected simultaneously.

To compute orientation (attitude), the sensor device provides its vector with respect to gravity and vector with respect to compass heading. Using the two vectors, an orientation with respect to Earth can be computed (an absolute orientation for this case). The vectors are provided by the accelerometer and magnetometer respectively. In practice, the two sensors alone will produce a noisy attitude result because the accelerometer is subject to the random vibrations that occur when worn, and both do not detect fast changes in orientation. A method to correct both shortcomings is to combine another type of sensor data, in this case from a gyroscope. Gyroscope data is used for fast and extreme changes in orientation, while the accelerometer and magnetometer provide the base absolute heading with respect to Earth. This is known as sensor fusion.

There are sensor units that may satisfy the Bluetooth LE and the attitude computation requirements. In one example, Texas Instruments (TI) Sensor Tag development kits are used for development (Mk 1 sensors). These units have a 3-axis accelerometer, 3-axis magnetometer, 3-axis gyro and Bluetooth LE radio and stream their sensor data over a Bluetooth LE connection at a rate of 25 hz. Using these sensors, a "state model" of the risk assessment system can be implemented, along with a Bluetooth communications programming library, and implementation and adaptation of 2 sensor fusion algorithms for testing.

Linear Quadratic Estimation may be used to combine multiple types of noisy and/or drifting sensor data. This decreases the inaccuracies of each individual sensor, and is the most mathematically optimal filter and was investigated for use. However, the much simpler Complimentary Filter process may also provide sensor fusion and may have less computational requirements. Given the desire to enable real-time analysis on mobile devices that have finite computational capacity, the Complimentary Filter process is preferably used.

A prototype app was developed for iPad which served as a test-bed for the integration of the Bluetooth communications library, sensor streaming, attitude calculation and state analysis. Through testing of the system, it became apparent that the TI Sensor Tag development kits would not have the capability to serve further development of the system because they did not permit adjustment of the streaming rate (locked at 25 hz), lost data packets when streaming from more than one sensor on a device (3 sensors are needed for sensor fusion), and the magnetometer was only accurate enough for a general north heading while accurate attitude calculations use accurate compass readings.

Replacement sensor candidates may be Hexiwear Kinetis, Mbient Lab Metawear and Stt-Systems Inertial Motion. Hexiwear Kenetis may be chosen due to its open platform i.e. the Firmware for the sensor was available and open-source and permitted programming within a wide range of capabilities. The units are also low cost and possessed potentially useful features such as OLED display and haptic feedback. The use of this sensor required modification of the Bluetooth communications programming library to accommodate the different command interface from the previous sensors.

Programming work may enable the iPad application to use several different machine learning techniques to identify the posture and orientation of the person wearing the sensors, which would, in-turn, enable the allocation of numerical values against risk phrases drawn from the Australian Model Code of Practice, i.e. the equivalent of populating a risk assessment template.

Two example machine learning algorithms are: (1) a shallow neural network and (2) a support vector machine. Both were tested in three configurations: (1) raw sensor data being fed into the algorithm; (2) sensor attitude being fed into the algorithm and; (3) assessment criteria items being fed in to the algorithm. In principle, the algorithm looking at the complete sensor data would provide the most consistent detection of states, however in practice there were problems with false positives tracking the transitions of states and confusion between similar states. With more opportunity for the collection of training data to improve the machine learning models, these problems may be able to be resolved, however with the data and resources at hand, the configuration of the machine learning algorithm analysing the degrees of the assessment criteria items produced the most consistent detection and tracking.

To allocate numerical values, the app would be able to identify when items in the risk assessment occur, record their values and durations, and keep track of them. For example, for the bending and twisting section in a risk assessment, the app needs to identify that both a bend and twist are occurring (the machine learning aspect) and determine the magnitude of the movement and the duration (e.g. >40 degrees for over 2 minutes). For the identification, the system needed a number of reference data for the various criteria.

In some cases, the CPU on the sensor devices may not be powerful enough to stream data from 5 units at the required rate. Although it was theoretically possible to disable other sensors and services on the device consuming CPU cycles, the design of the system was such that that the drivers for the sensors were interdependent and this meant significant work would be required to change the configuration.

Mbient Lab released a new sensor unit which incorporated the sensor fusion on-chip, reducing the amount of data that needed to be streamed and recorded, had enormous internal storage for recording sensor data, and had a very fast CPU. Due to the difficulty of modifying the mk2 sensor firmware, the system may be changed to incorporate the Metamotion R sensors (mk3). The change is reflected by simplification of the Bluetooth programming library and modification to the detection system.

Refinements to the state recognition and processing algorithms may be continuous to improve the accuracy and consistency, along with further training of the machine learning algorithms to improve the state recognition for more varied combinations of assessment criteria. Magnetometer calibration may be performed every 30 to 40 minutes and also when environments change. A sensor firmware change may allow continuous adaptive calibration solving the calibration issues (mk4 sensors).

In addition to the sensors and the software behind the app, there is provided a user interface with the app to enable intuitive operation of the system and to display risk assessments live when the app is connected to the sensors and the task is being performed. The latter feature is based on a desire to use the system in education and training i.e. allow workers, supervisors, managers and health and safety personnel to see what elements of tasks expose people to elevated risk levels and facilitate discussions around risk control measures.

The consequence scoring element of the risk estimation calculation may be based on extensive injury clinical and claims data. This method enables the provision of ranked scores based on type of injury risk and enables use alongside other Work Health & Safety risk-scoring.

Prototype Development & Research

With the mk4 sensors and refined test app the first on-site visit for pilot trialling was scheduled. In preparation for the first on-site pilot trials, laboratory verification was conducted by fitting subjects with sensors who undertook a range of basic movements and adopted a variety of positions and orientations that were compared with reports generated by the app. Repeated trials enabled machine learning and validation of the app.

First Onsite Pilot (Trial)

The first mine site piloting was conducted at BMA's open cut coal mine, Peak Downs. The aim was to gather data for subsequent verification through ergonomist task observation and assessment. Six maintenance tasks were observed and assessed:

Moving Wheeled Platform & Steps Unit-Truck Maintenance Workshop
Roller Change-Wash Area-ROM Conveyors-Preparation Plant-Processing Plant
Scaffolding Equipment and materials handling-Preparation Plant
Moving and Emptying Bins-Truck Maintenance Workshop
Under truck Inspection-Truck Maintenance Workshop
Filter Change-Truck Maintenance Workshop Sensors were attached to a range of mine personnel undertaking the tasks. The subjects were of different ages and body types, one female, five males. Sensors were attached to the back, hip, head and wrist of the workers enabling assessment of discrete as well as combined movements such as simultaneous bending and twisting.

The sensors transmitted data to the App where the environment allowed, while simultaneously logging the sensor data to their internal memory. This enabled real time assessments including video collection as well as post hoc data analysis where workers were remote to the researchers. The app generated states were used to generate risk assessment reports.

Following the mine-site trial, expert ergonomist assessment of the collected data was undertaken for the purposes of validation and development of the app.

The sensors were subject to coal dust, coal mud, dirty and clean water and hot dirty engine oil and all functioned normally and it was found that battery life far exceeded needs. It was found that the posterior placement of the hip sensor meant that it got caught and pulled off in two instances of it being used and therefore re-positioning needed to be considered and a limitation was the use of the iPad in the wet areas but the data logging feature means that post hoc analysis is possible.

The data analysis from the first on-site visit data revealed several areas for improvement in the system; the timecode syncing between the sensors was not implemented correctly in firmware. This resulted in the recording of differing timecodes that led to significant amount of time being added to the analysis and synchronisation work. This problem was resolved by the manufacturer after changes and updates to the sensor firmware were requested. More significantly, it was apparent that the standard risk assessment criteria were not suitably defined for the automated system to make use of. This would be the major point of development leading up to the next stage.

First Onsite Pilot (Trial) Analysis

During the first onsite piloting trial there were short periods of automated data gathering with simultaneous videoing of the tasks. Data and vision/video capture were limited by the nature and circumstances of the tasks and the inability to observe the tasks throughout their duration given worker mobility and accessibility.

The videoed periods of the tasks with simultaneous auto data collection were typically less than two minutes with some up to five minutes. Video segments suitable for ergonomist analysis ranged from 20 seconds to two minutes in length. The video segments presented discrete sets of movements, postures and task actions. This made the ergonomist's work of recognising and categorising movement and posture and allocating frequency and repetition scores relatively straight forward.

It became apparent that, while there was general agreement between the automated (auto) and ergonomist (ergo) analyses of the tasks, there were discrepancies. It is likely that the differences between auto and ergo analyses are associated with the way in which the ergo brings to the process their experience of analysing a range of observed tasks and makes assumptions. It appears that the ergo assumptions increase with the quantum of repetitive and sustained categorised data. Where longer periods of work are observed and/or when the work observed has intense periods of movement, a variety of postures, and repetitive and sustained data generation across multiple risk categories, it is likely that the ergo allocates risk categories on the basis of the initial and the most clearly observable movement, postures, actions and loads. From this, the ergo estimates frequencies and durations. Contrastingly, the auto system undertakes objective, accurately quantified measurement of action durations and occurrences against elapsed time.

It is thought that the ergo analysis is subject to "Serial position effect". This is the tendency of a person to recall the first and last items in a series best, and the middle items worst. It has been found that recall accuracy varies as a function of an item's position within a study list. When asked to recall a list of items in any order (free recall), people tend to begin recall with the end of the list, recalling those items best (the recency effect). Among earlier list items, the first few items are recalled more frequently than the middle items (the primacy effect).

The learning from the ergo-auto comparisons and the practical elements of the onsite trials led to further software and hardware refinements in preparation for a second workplace trial.

Development for Industry Trial

The comparison of machine versus human risk assessments at the completion of the first on-site trials identified a range of assumptions that are made in the human use of the Australian Model Code of Practice and other risk assessments checklists. Risk assessment in general is a highly subjective process. In respect to the risk phrases within the Australian Model Code of Practice assessment and like processes, it is apparent that the ergonomist makes many intuitive assumptions, uses experience and knowledge of a process or that of similar tasks and introduces prejudice. An automated system is, conversely, objective and completes assessments solely based on data received regarding the position of the sensors in space.

Work was therefore undertaken to define (at a low-level) what constitutes a trigger for the assessment state criteria. For example; consider the isolated assessment item of sustained or repetitive bending forward. There are 3 criteria "degrees" of the bending forward state:

Bending forward less than 20°
Bending forward>=20 AND<45°
Bending forward>=45 AND 90°
Bending forward>=90°

Sustained may be defined as being held for 30 seconds or more continuously, repetitive is defined as being performed 3 or more times per minute.

Additionally, the assessment used by both the machine (auto) and human (ergo) in this project defines the required exposure ratings as:

Very rare:
(<30 minutes over the whole shift) OR
(<5 minutes at a time)
Rare:
(>=30 AND<60 minutes over the whole shift) OR
(>=5 AND<15 minutes at a time)
Unusual:
(>=60 AND<90 minutes over the whole shift) OR
(>=15 AND<30 minutes at a time)
Occasional:
(>=90 AND<120 minutes over the whole shift) OR
(>=30 AND<45 minutes at a time)
Frequently:
(>=120 AND<240 minutes over the whole shift) OR
(>=45 AND<60 minutes at a time)
Continuously:
(>=240 minutes over the whole shift) OR
(>=60 minutes at a time)

The system was identifying and tracking this state with high accuracy and consistency, as represented in FIG. 1. This example case uses 10 second time interval blocks for ease of visualisation (the system was sampling at 0.01 second blocks). The bend forward from time index 7 to 13 met the criteria for sustained (30 seconds or more), however the degree at which the bend would be tracked as was not defined.

Figure 2:
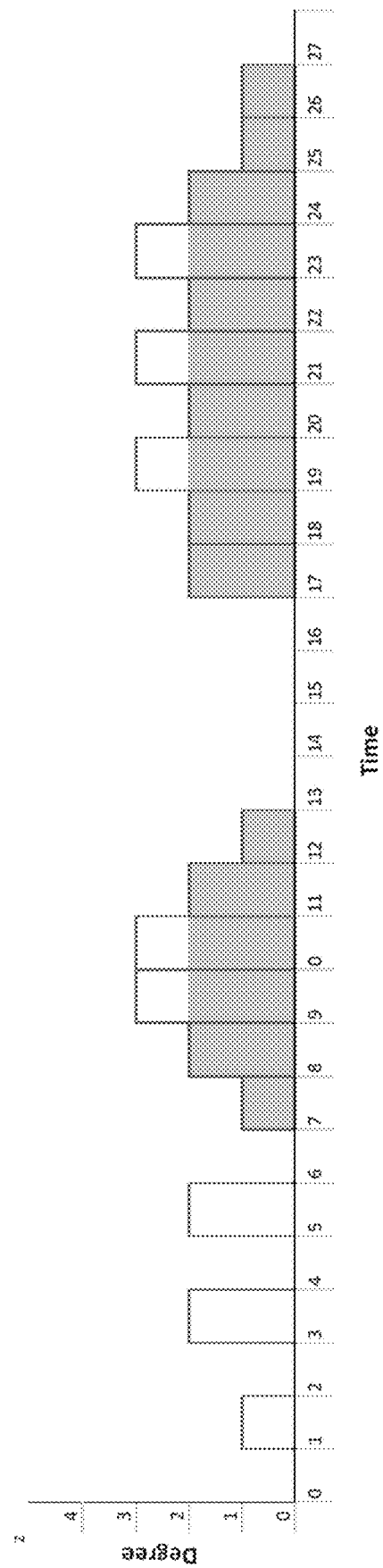
FIG. 2 shows sustained blocks that meet a criteria in shading.

A higher-degree-inclusive definition may be used as follows:

higher degree time would contribute to adjacent lower degree sustained time if the higher degree had not been sustained for 30 seconds or more.

if the higher degree did last long enough to trigger a sustained block, then lower degrees that are adjacent to the sustained block will contribute to total time for their respective degrees FIG. 2 shows the sustained blocks that meet the criteria in green. Degree 3 at time index 9-11 does not meet the 30 second requirements, therefore it gets included in the next highest adjacent degree: degree 2 in this case. Now degree 2 lasts from time index 8-12, which does meet the 30 second sustained criteria, so it contributes 40 seconds to the total time for sustained bending forward at degree 2. Also note that time indexes 7-8 and 12-13 are showing as meeting the sustained criteria, as they are adjacent to a higher degree sustained trigger block.

Figure 3:
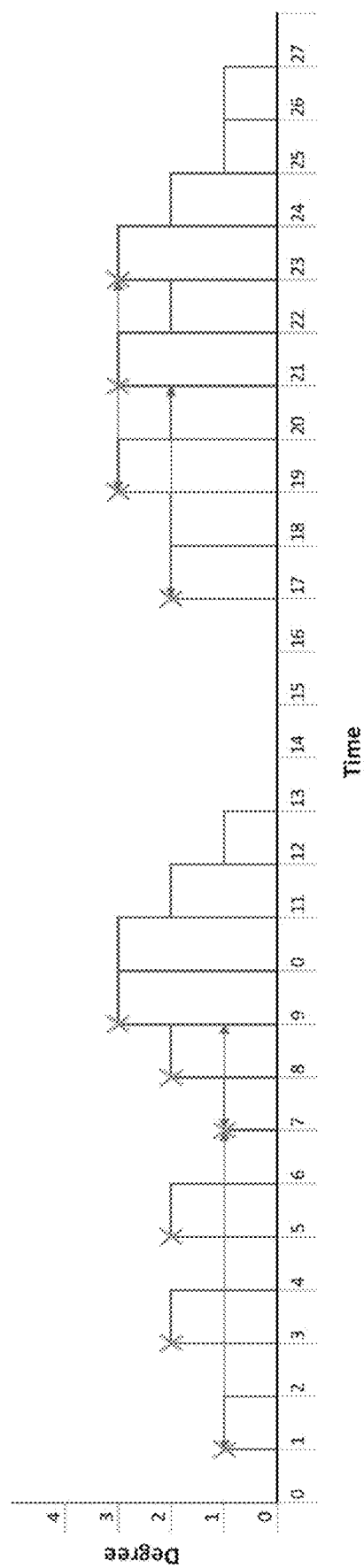
FIG. 3 shows transitions between degrees.

For the repetitive detection, a repeat event was defined as the transition from some degree to a higher degree (shown as red X in FIG. 3). When 3 events are detected within one minute (the criteria for repetitive motion), the degree of the repetitive event is determined by the lowest degree of the repeat event group (shown ad horizontal lines in FIG. 3). Repeat events can overlap over the same time interval (see time interval 17-21 and 19-23 in FIG. 3), when this occurs the higher degree is used for that time interval's contribution to the total time. In the example, the degree and time contribution for the bend from time index 17-27 would be 20 seconds in degree 2, and 40 seconds in degree 3.

A similar approach was defined for the combination of sustained and repetitive: after detection of the blocks that meet the repetitive or sustained criteria, the method used with the repetitive criteria is used to combine the sustained and repetitive blocks. The repetitive and sustained degrees and times for the bend from time index 17-27 would be 40 seconds in degree 3, 40 seconds in degree 2 and 20 seconds in degree 1 (4, 4, 2 time samples respectively in the example).

Figure 4:
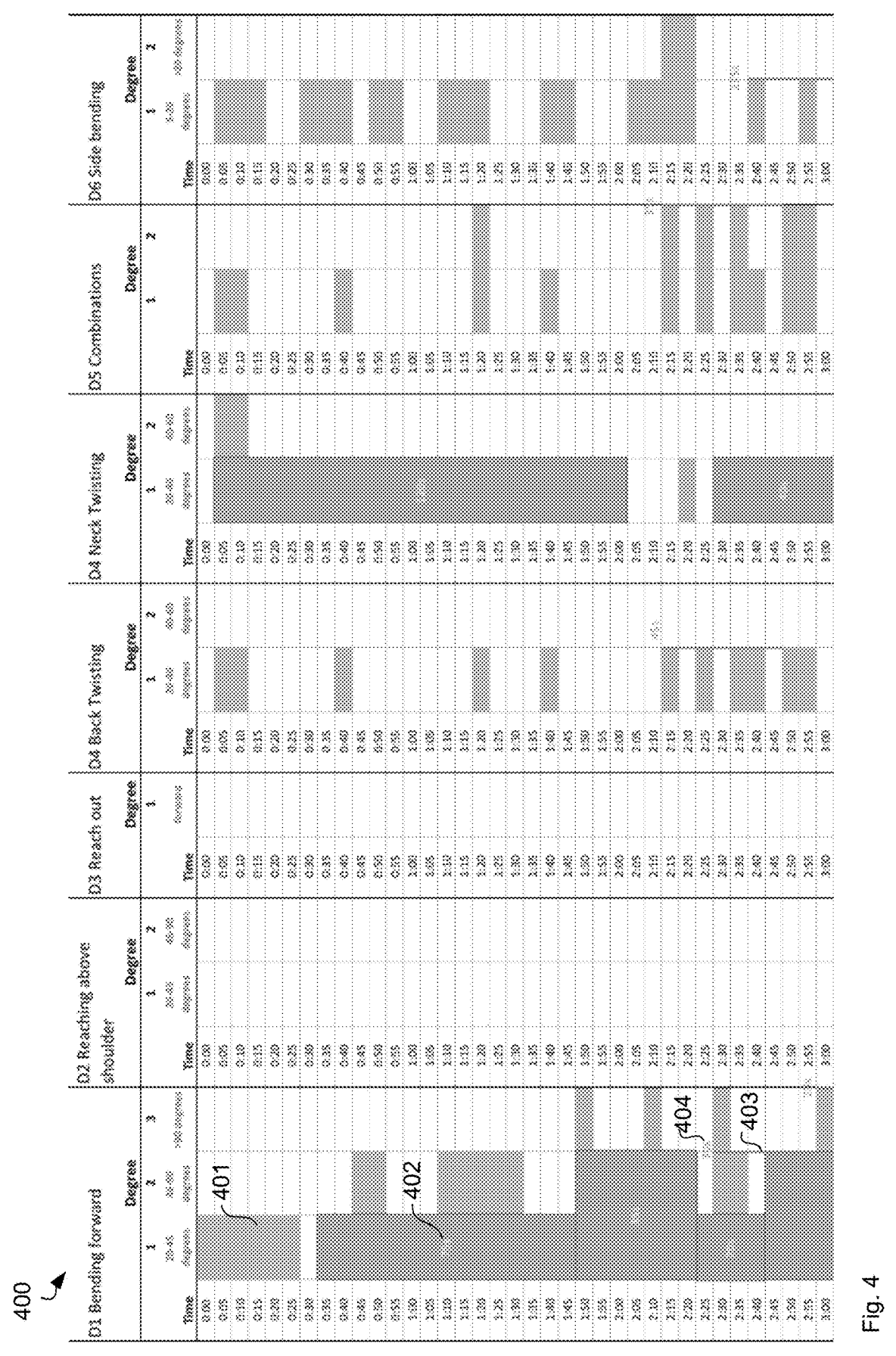
Figure 4:
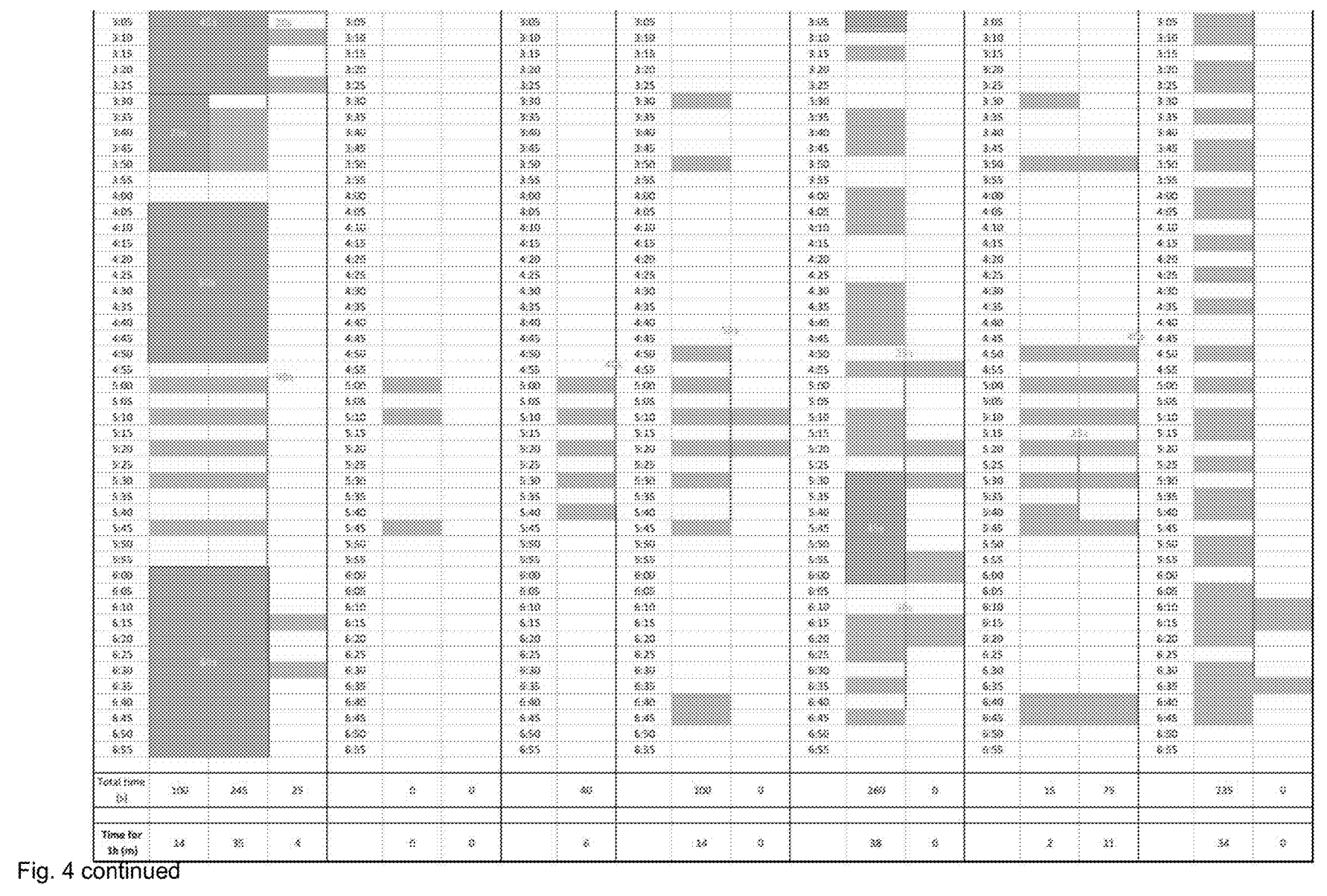

FIG. 4 illustrates a graphical indication 400 of the degree to which each movement pattern occurred over time (at 5 s time steps in this case). In this case, there are six movement patterns (D1-D6) and each pattern has three degrees (1-3). In this case, "degree" relates to an angle of the worker's body but may also mean "intensity". When a particular degree is detected, the area corresponding to the pattern, degree and time slot are filled in solid colour 401.

For longer continuous occurrences of movement patterns, the actual duration is displayed within the filled area 402. If the pattern is interrupted by not more than a predefined period of time, such as 5 seconds, the individual blocks may be connected by a vertical line 403 and a numerical annotation 404 indicating the duration of the movement pattern at a particular intensity disregarding the short interruptions.

After discussion and definition of the risk assessment, the changes to the algorithms were implemented in preparation for the second on-site visit. Improvements to firmware and the Bluetooth programming library allowed the full five sensors to be used at once, compared to the four sensors for the first on-site visit.

Second Onsite Pilot (Trial)

A second site visit at BMA's open cut coal mine, Peak Downs was conducted. The aim was to gather data for subsequent verification through ergonomist task observation and assessment. Five maintenance tasks were observed and assessed:

Filling blast/shot holes
Worker role: Shot operator/shothand
Department/Work area: BMA Drill and Blast Crew
Changing bushes on Dragline electric motors-Dragline shutdown Worker role: Electrician
Department/Work area: Maintenance
Cleaning dragline-Dragline shutdown
Worker role: Cleaner
Department/Work area: Maintenance
Replacing lower pins on dragline bucket
Worker role: Boilermaker
Department/Work area: Maintenance
Cutting steel plate at ROM
Worker role: Boilermaker
Department/Work area: Maintenance Sensors were attached to five males of different ages and body types. Sensors were attached to the back, hip, head and both wrists of the workers enabling assessment of discrete as well as combined movements such as simultaneous bending and twisting.

Second Onsite Pilot (Trial) Analysis

A primary advantage for the second onsite test was to capture video (for ergonomic analysis) and gather sensor data for tasks of longer assessable and observable duration. This resulted in the majority (four of five) of the tasks analysed from the second onsite pilot trialling being from 12 to 18 minutes duration, and providing richer data than had previously been available. This permitted a comparison between the ergonomist and the automated system that had higher significant scoring.

Comparison between the sensor-detected states and the ergonomist analysed video footage of the tasks demonstrated close correlation; the automated system is following the risk assessment criteria precisely to generate the risk score. However, the risk-scores derived respectively from the automated assessment and the ergonomist assessment can differ in magnitude (see Tables 1-5), with the automated assessment generally scoring the same task slightly higher than the ergonomist. In each of four cases, both the auto and the ergo risk scores were in the same band i.e. delivered the same risk level descriptor and recommendation used in the Risk Score Guidelines shown in table 6.

An exception to agreement between the auto and ergo assessment was with respect to the filling blast shot holes task (Table 4). In this instance, the ergo score of the task was substantially higher than the auto score. The task involved the worker being stationary while swinging his arms for an extended period. The arm swing was similar to that usually associated with walking but in this case, was used to move a rope. The ergo scored the action based on it being a repetitious action for an extended period (score 100) while the auto scored the action based on it being similar to walking (score 0) i.e. the main contributor to the difference in scores is the limb & joints movements per minute category (D6h).

Having identified this discrepancy, the machine learning algorithm can be used to enable the auto system to use the absence of movements detected by the other sensors to detect non-walking activities. This will be developed during the extended post-project trials.

The existing risk assessment protocol is fundamentally based around the task in context of the work shift. As the tasks observed were specific, discreet tasks, with their frequency of occurrence throughout a person's shift unknown, both the scores from the automated system and the ergonomist were normalised to a 1 hour shift for comparison purposes. In the sense that the scores generated are risk score per hour of the task.

The ergo observation and analysis of the video footage demonstrated that ergonomist judgements of severity and significance increase as the volume of data increases. Simply put, humans are expert at dealing with a multitude of inputs by filtering to enable cognitive processing of what experience and training signify as important. This is particularly so in relation to the analysis of observed multiple repetitive and sustained actions over longer durations.

The automated system does not analyse data in the context of other tasks that it has analysed; instead it objectively analyses data input for each discrete task. While the criteria of the risk assessment methods are the same, the automated system feeds-forward into the risk assessment to obtain a risk score, whereas the ergonomist would appear to feed-back into the risk assessment to convey a risk score.

The automated system is consistent with itself between various tasks, which would seem to indicate that it can determine the level of risk and compare the level of risk for work activities, provided that the existing risk assessment criteria are comparable.

TABLE 1

Cleaning dragline risk assessment

| Assessment Category | Automated | Ergonomist |
|---|---|---|
| Repetitive or sustained | 91 | 74 |
| Heavy loads or high forces | 0 | 2.5 |
| Difficult or awkward loads | — | 0 |
| Vibration | 0 | 0 |
| Occupational overuse syndrome | — | 5 |
| Total | 91 (substantial) | 81.5 (substantial) |

TABLE 2

Cutting steel plate risk assessment

| Assessment Category | Automated | Ergonomist |
|---|---|---|
| Repetitive or sustained | 59.5 | 45 |
| Heavy loads or high forces | 10.0 | 16.5 |
| Difficult or awkward loads | — | 2.5 |
| Vibration | 0 | 0 |
| Occupational overuse syndrome | — | 0 |
| Total | 92 (substantial) | 64 (possible) |

TABLE 3

Replacing dragline bucket pins risk assessment

| Assessment Category | Automated | Ergonomist |
|---|---|---|
| Repetitive or sustained | 52.5 | 35.0 |
| Heavy loads or high forces | 25 | 24.5 |
| Difficult or awkward loads | — | 0 |
| Vibration | 0 | 0 |
| Occupational overuse syndrome | — | 8.0 |
| Total | 77.5 (substantial) | 67.5 (possible) |

TABLE 4

Filling blast shot holes risk assessment

| Assessment Category | Automated | Ergonomist |
|---|---|---|
| Repetitive or sustained | 36.5 | 149.5 |
| Heavy loads or high forces | 7.5 | 2 |
| Difficult or awkward loads | — | 0 |

TABLE 4-continued

Filling blast shot holes risk assessment

| Assessment Category | Automated | Ergonomist |
|---|---|---|
| Vibration | 0 | 0 |
| Occupational overuse syndrome | — | 0 |
| Total | 44.0 (possible) | 151.5 (substantial) |

TABLE 5

Changing bushes risk assessment

| Assessment Category | Automated | Ergonomist |
|---|---|---|
| Repetitive or sustained | 50 | 41 |
| Heavy loads or high forces | — | 3.5 |
| Difficult or awkward loads | — | 7.5 |
| Vibration | — | 0 |
| Occupational overuse syndrome | — | 0 |
| Total | 50 (possible) | 52 (possible) |

TABLE 6

Risk score guidelines

| Risk Score | Recommendation |
|---|---|
| >400 | Very High Risk; Discontinue Operation |
| 200-400 | High Risk; Immediate Correction Required |
| 70-200 | Substantial Risk; Correction Needed |
| 20-70 | Possible Risk; Attention Indicated |
| <20 | Risk; Perhaps Acceptable |

The operation of the app is intuitive, enables simple presentation of risk assessment data and it facilitates discussion with site personnel. Task management, cloud syncing of data, and the systems for simultaneous video recording (at the same time as the sensor data were developed and implemented.

An automated musculoskeletal injury risk assessment system that employs wearable sensors paired with an app has been described. The app works on phones and tablets using a developed machine learning system to analyse data and present it on intuitive screens in simple report formats.

The risk assessment method employed by the application is based on and is closely aligned to the Australian Model Code of Practice-Hazardous Manual Tasks 2016 and its predecessor codes, guides and national standard. This method has been extended to address a factor that limits application by both expert and casual users; the consequence scoring in the risk estimation calculation has been populated using extensive injury clinical and claims data. This standardised method results in the provision of ranked scores based on type of injury risk and enables use alongside other Work Health & Safety risk-scoring.

The risk assessment process was verified by human expert (ergonomist) observation and assessment of the manual handling tasks being app-assessed. Comparison between the sensor-detected states and the ergonomist analysed video footage of the tasks demonstrated close correlation; the automated system is following the risk assessment criteria precisely to generate the risk score and therefore brings a high degree of reliability to the assessment process.

The risk-scores derived respectively from the automated assessment and the ergonomist assessment can differ in magnitude but over the limited trials completed, the ergo and app risk scores were in the same band i.e. delivered the same risk level descriptor and recommendation. An exception to this was a specific task that was assessed where the subject was stationary while swinging his arms for an extended period and the two assessments disagreed. Having identified this discrepancy, the machine learning algorithm can be modified and developed during the extended post-project trials.

The computing rate of the app makes it better able to quantify repetitious movement than the human.

There is provided an app that pairs with wearable sensors to enable automated MSD risk assessments. The solution disclosed herein may be applicable in the production of product packages for the coal mining industry nationally, the metalliferous sector nationally, the international market and other industries. Product packages may include the application and sensors, support and training. The electronic components of the package may be SIMTARS certified for underground use.

Figure 5:
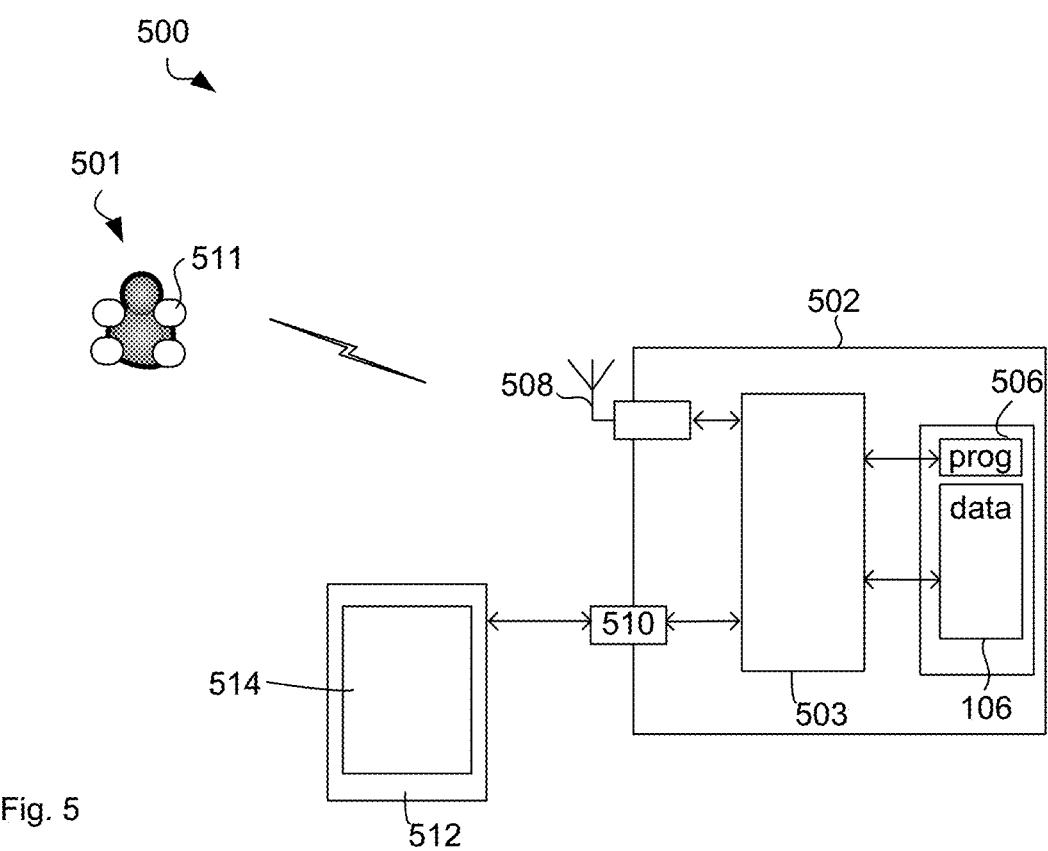
FIG. 5 illustrates a system for monitoring movements of a worker.

FIG. 5 illustrates a system 500 for monitoring movements of a worker 501. The system 500 comprises a mobile device 502 with a processor 503 connected to a program memory 504, a data memory 506, a communication port 508 and a user port 510. System 500 also comprises inertial sensors 511. The program memory 504 is a non-transitory computer readable medium, such as a hard drive, a solid state disk or CD-ROM. Software, that is, an executable program stored on program memory 504 causes the processor 503 to perform the method in FIG. 6, that is, processor 503 receives sensor data, identifies movement patterns and calculates a risk score. The term "determining a risk score" refers to calculating a value that is indicative of the risk score. This also applies to related terms.

The processor 503 may then store the risk score on data store 506, such as on RAM or a processor register. Processor 503 may also send the determined risk score via communication port 508 to a server, such as a whole-of-mine control centre.

The processor 503 may receive data, such as inertial sensor data, from data memory 506 as well as from the communications port 508 and the user port 510, which is connected to a display 512 that shows a visual representation 514 of the risk score to a user, which may be worker 501, a supervisor or other person. In one example, the processor 503 receives sensor data from sensors via communications port 508, such as by using a low-energy Bluetooth.

In one example, the processor 503 receives and processes the sensor data in real time. This means that the processor 503 determines the sensor data every time sensor data is received from sensors 511 and completes this calculation before the sensors 511 send the next data update. In other examples, real-time means that the processing time or delay is small relative to the activity by the worker 501, such as the perceived processing is contemporaneous to the activities. This may be a delay of less than 10 s or less than 1 s.

Although communications port 508 and user port 510 are shown as distinct entities, it is to be understood that any kind of data port may be used to receive data, such as a network connection, a memory interface, a pin of the chip package of processor 503, or logical ports, such as IP sockets or parameters of functions stored on program memory 504 and executed by processor 503. These parameters may be stored on data memory 506 and may be handled by-value or by-reference, that is, as a pointer, in the source code.

The processor 503 may receive data through all these interfaces, which includes memory access of volatile memory, such as cache or RAM, or non-volatile memory, such as an optical disk drive, hard disk drive, storage server or cloud storage. It is to be understood that any receiving step may be preceded by the processor 503 determining or computing the data that is later received. For example, the processor 503 determines sensor data and stores the sensor data in data memory 506, such as RAM or a processor register. The processor 503 then requests the data from the data memory 506, such as by providing a read signal together with a memory address. The data memory 506 provides the data as a voltage signal on a physical bit line and the processor 503 receives the sensor data via a memory interface. As described above, sensors 511 may comprise processing capability and pre-process the sensor data or extract features from the sensor data. The extracted features are still referred to as inertial sensor data herein because they are based on the original raw measurements.

It is to be understood that throughout this disclosure unless stated otherwise, nodes, edges, graphs, solutions, variables, scores and the like refer to data structures, which are physically stored on data memory 506 or processed by processor 503. Further, for the sake of brevity when reference is made to particular variable names, such as "period of time" or "risk score" this is to be understood to refer to values of variables stored as physical data in computer system 500.

Figure 6:
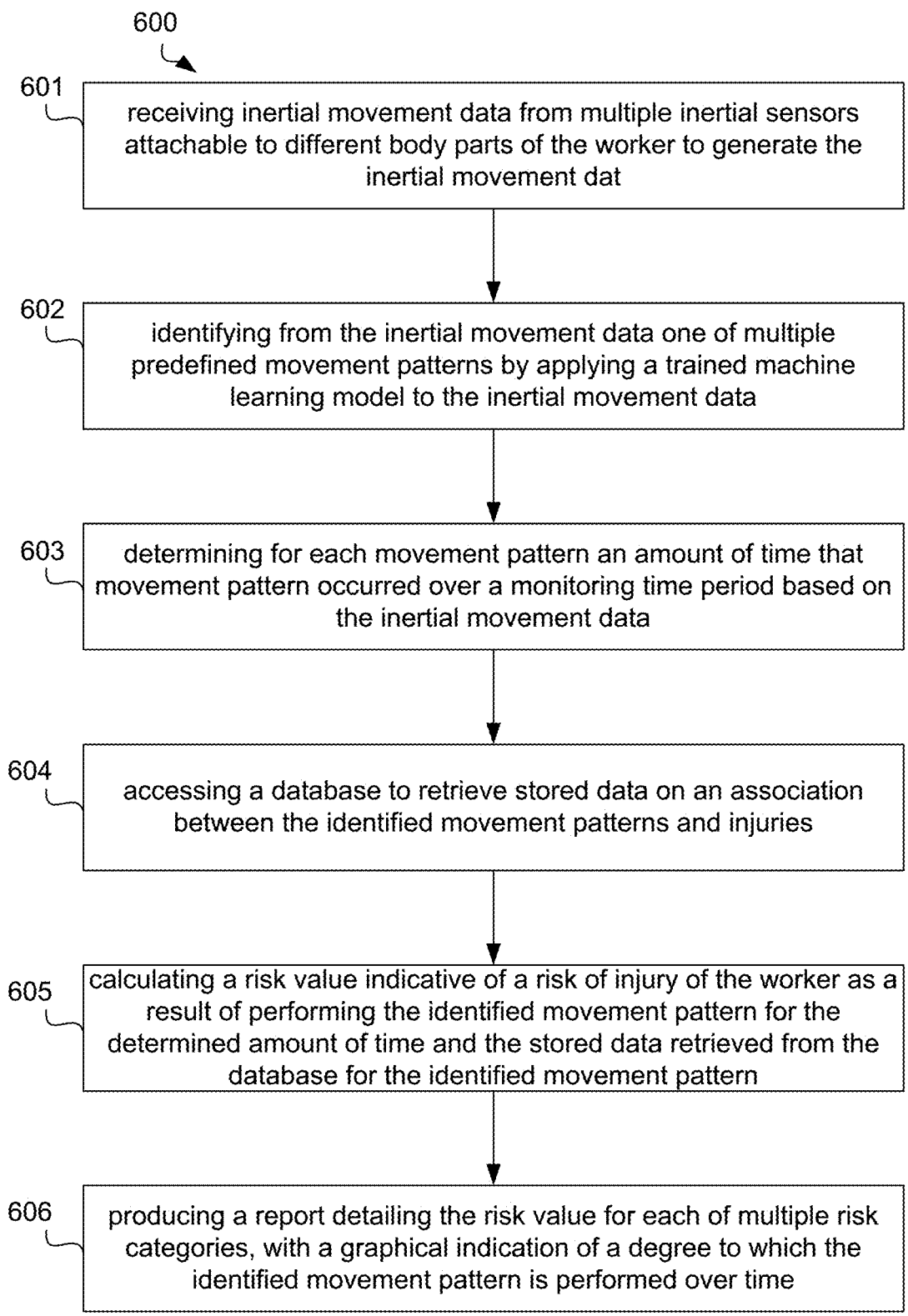
FIG. 6 illustrates a method for monitoring a worker.

FIG. 6 illustrates a method 600 as performed by processor 503 for monitoring a worker. FIG. 6 is to be understood as a blueprint for the software program and may be implemented step-by-step, such that each step in FIG. 6 is represented by a function in a programming language, such as C++ or Java. The resulting source code is then compiled and stored as computer executable instructions on program memory 504.

It is noted that for most humans performing the method 600 manually, that is, without the help of a computer, would be practically impossible. Therefore, the use of a computer is part of the substance of the invention and allows performing the necessary calculations that would otherwise not be possible due to the large amount of data and the large number of calculations that are involved.

Method 600 commences by receiving 601 inertial movement data from multiple inertial sensors 511 attachable to different body parts of the worker to generate the inertial movement data as described above. This may involve pre-processing by the sensor 511 and low-power Bluetooth or other technologies. Next, processor 503 identifies 602 from the inertial movement data one of multiple predefined movement patterns. This is achieved by applying a trained machine learning model to the inertial movement data, such as a support vector machine. Then, processor 503 determines 603 for each movement pattern an amount of time that movement pattern occurred over a monitoring time period based on the inertial movement data and accesses 604 a database to retrieve stored data on an association between the identified movement patterns and injuries. Processor 503 further calculates a risk value indicative of a risk of injury of the worker as a result of performing the identified movement pattern for the determined amount of time. This calculation is based on the stored data retrieved from the database for the identified movement pattern. In other words, processor 503 accesses the database and retrieves for each determined movement pattern and time a weight or other factor from the database and combines these factors into the overall risk value. Finally, processor 503 produces a report detailing the risk value for each of multiple risk categories, with a graphical indication of a degree to which the identified movement pattern is performed over time.

In further examples, each sensor outputs:
absolute orientation in space via sensor fusion of accelerometer, gyro, and
magnetometer
altitude
impacts In some examples, analysis and comparison of the orientations and altitudes of the sensors are used to determine the various positions of body regions (lower body/hip, upper body, head and wrists). A state vector machine (SVM) may be used to "combine" the orientation and altitudes for the wrists to determine the reaching state. Impacts may be tracked independently for all body regions.

The SVM may be trained on existing movement data collected from movements of various subjects with attached sensors. The sensor data is then manually annotated at multiple points in time and then used as learning samples for the different movement patterns. About 50 learning samples per movement pattern may be used in one example. The SVM supplements the orientation data from the body movements. In particular, a Kalman filter is used to fuse accelerometer, magnetometer and gyroscope into an absolute orientation/pose (heading/pitch/yaw) of the sensor in space. For some orientations, there are different possibilities on what the state (i.e. movement pattern could be). For example, if the wrist orientation is up, it is not known whether the wrist is above the head or not, which is important for the reaching up state. For those cases, the SVM processes data from multiple sensors, such as one on each wrist, torso and neck.

The orientation of the sensors feeds into machine leaning SVM which then outputs the state. In one example, the SVM training and evaluation is performed by Google's tensor flow library executed on the mobile device.

The risk score can be reported at the end of the task, where the score is based on exposure time. A video overlay combines the video of the task with the state of the system as reported as a progressing timeline alongside the video. When streaming data in real-time, the timeline of the state progresses in real-time. After the conclusion of the task, the video and state timeline can be "scrubbed through" together and saved as a distributable video.

In one example, the mobile device application is further configured to receive video data from a video camera, which may be a camera integrated into the mobile device 502. Processor 503 time-aligns the video data with the inertial sensor data in the sense that the frames of the video are synchronised with the sensor samples. This can be achieved by reading time stamps from the sensor data and the video. Processor 503 then creates a display of the video with an indication of identified movement patterns for each frame of the video. The indication of identified movement patterns may be a graphical indication of a degree to which the identified movement pattern is performed at that frame.

For example, the video may be displayed next to a table similar to the table shown in FIG. 4 which shows the degree to which each movement pattern occurred over time (at 5 s) time steps in this case. The graphical indication is akin to a bar chart or column chart indicating the degree to which the identified movement pattern is performed at that frame or continuous subset of frames. Processor 503 may add a horizontal line at a particular time that relates to the current frame of the video. In this sense, as the video plays, the horizontal lines moves downward in FIG. 4. If the user decides to rewind the video, the horizontal lines moves upward.

The video display may also comprise a slider to move through the frames of the video (i.e. scrubbing). This action then also synchronously moves the horizontal line upwards or downwards depending on the movement on the slider through the indications of identified movement patterns in FIG. 4. In other words, the slider moves both the horizontal line in FIG. 4 as well as the displayed video time synchronously. This way, the user can conveniently move to a part of the video where movements occurred to a high degree, for example.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A system for assessing a risk of musculoskeletal disorder caused by repetitive or sustained movements of a worker, the system comprising:
multiple inertial sensors attachable to different body parts of the worker to generate inertial movement data;
a mobile device application configured to
receive the inertial movement data from the inertial sensors;
classify the inertial movement data into one of multiple predefined movement patterns by applying a trained machine learning model to the inertial movement data;
classify the inertial movement data into one of multiple predefined degree categories, each degree category representing a range of movement angle, to which the identified movement pattern is performed;
determine, for the identified movement pattern, duration the identified movement pattern occurred at that degree over a monitoring time period based on the inertial movement data;
accessing a database to retrieve stored data on an association between the identified movement patterns and injuries;
calculate a risk value indicative of a risk of injury of the worker as a result of performing the identified movement pattern using the determined duration at the determined degree and the stored data retrieved from the database for the identified movement pattern; and
produce a report detailing the risk value for each of multiple risk categories, with a graphical indication of the degree to which the identified movement pattern is performed over the monitoring time.

2. The system of claim 1, wherein the mobile device application is further configured to:
receive video data;
time-align the video data with the inertial movement data; and
create a display of the video data with an indication of the identified movement patterns for each frame of the video.

3. The system of claim 2, wherein the indication of identified movement patterns comprises the graphical indication of the degree to which the identified movement pattern is performed at each frame.

4. The system of claim 3, wherein the graphical indication comprises a bar chart or column chart indicating the degree category representing the range of movement angle to which the identified movement pattern is performed at a given frame or a continuous subset of frames.

5. The system of claim 2, wherein the video display comprises a slider to move through each frames of the video that also synchronously moves through a respective indication of the identified movement patterns for each frame of the video.

6. The system of claim 1, wherein the applying of the trained machine learning model comprises extracting features from the inertial sensor data and the applying of the trained machine learning model for the extracted features.

7. The system of claim 6, wherein the extracted features comprise an orientation of each sensor of the multiple inertial sensors.

8. The system of claim 1, wherein the trained machine learning model comprises a support vector machine.

9. The system of claim 1, wherein the inertial sensors comprise accelerometers or gyroscopes or both.

10. The system of claim 1, wherein the system further comprises magnetometers or altimeters or both and the steps of receiving, identifying, determining and calculating are performed on sensor data from the magnetometers or altimeters or both.

11. The system of claim 1, wherein identifying the movement pattern comprises determining an orientation of each sensor and identifying the movement pattern based on the orientation of each sensor of the multiple inertial sensors.

12. The system of claim 1, wherein the sensors are grouped into regions of the worker's body and the one of the movement patterns is identified for each region of the regions of the worker's body.

13. The system of claim 1, wherein a data collecting device is configured to detect impacts based on the inertial sensor data and calculating the risk value based on the detected impacts.

14. The system of claim 1, wherein the stored data on the association between the identified movement pattern and injuries comprises injury medical data or medical claims data or both.

15. A method for assessing a risk of musculoskeletal disorder caused by repetitive or sustained movements of a worker, the method comprising:
receiving inertial movement data from multiple inertial sensors attachable to different body parts of the worker to generate the inertial movement data;
classify the inertial movement data into one of multiple predefined movement patterns by applying a trained machine learning model to the inertial movement data;
classify the inertial movement data into one of multiple predefined a degree categories, each degree category representing a range of movement angle, to which the identified movement pattern is performed;
determining, for the identified movement pattern, a duration the identified movement pattern occurred at that degree over a monitoring time period based on the inertial movement data;
accessing a database to retrieve stored data on an association between the identified movement patterns and injuries;
calculating a risk value indicative of a risk of injury of the worker as a result of performing the identified movement pattern using the determined duration at the determined degree and stored data retrieved from the database for the identified movement pattern; and
producing a report detailing the risk value for each of multiple risk categories, with a graphical indication of the degree to which the identified movement pattern is performed over the monitoring time.

16. The system of claim 1, wherein the association comprises a factor indicative of a consequence scoring derived from injury clinical and claims data.

17. The system of claim 16, wherein the mobile device application is further configured to calculate the consequence scoring using injury clinical and claims data.

* * * * *